United States Patent
Kostrzewski

(10) Patent No.: US 11,497,572 B2
(45) Date of Patent: *Nov. 15, 2022

(54) MEDICAL DEVICE ADAPTER WITH WRIST MECHANISM

(71) Applicant: Covidien LP, Mansfield, MA (US)

(72) Inventor: Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 508 days.

This patent is subject to a terminal disclaimer.

(21) Appl. No.: 16/542,668

(22) Filed: Aug. 16, 2019

(65) Prior Publication Data

US 2019/0365492 A1 Dec. 5, 2019

Related U.S. Application Data

(60) Continuation of application No. 15/049,651, filed on Feb. 22, 2016, now Pat. No. 10,390,897, which is a
(Continued)

(51) Int. Cl.
*A61B 34/00* (2016.01)
*A61B 17/072* (2006.01)
(Continued)

(52) U.S. Cl.
CPC ........ *A61B 34/70* (2016.02); *A61B 17/07207* (2013.01); *F16D 1/08* (2013.01);
(Continued)

(58) Field of Classification Search
CPC .............. A61B 34/70; A61B 17/07207; A61B 2034/305; F16D 1/08; F16H 35/008; Y10T 403/32008

See application file for complete search history.

(56) References Cited

U.S. PATENT DOCUMENTS 562,173 A 6/1896 Daniels
942,545 A 12/1909 Colidge
(Continued)

FOREIGN PATENT DOCUMENTS

AU 2008229795 A1 4/2009
CA 2451558 A1 1/2003
(Continued)

OTHER PUBLICATIONS

Extended European Search Report corresponding to International Application No. EP 15 17 3803.6 dated Nov. 24, 2015.
(Continued)

*Primary Examiner* — Julian W Woo
(74) *Attorney, Agent, or Firm* — Carter, DeLuca & Farrell LLP

(57) ABSTRACT

A surgical device adapter for coupling an end effector to a surgical device includes: a proximal joint housing that is couplable to the surgical device; a middle joint housing pivotally coupled to the distal end of the proximal joint housing; and a distal joint housing pivotally coupled to the distal end of the middle joint housing. The middle joint housing is pivotable about a first pivot axis defined between the proximal joint housing and the middle joint housing. The distal joint housing is couplable to the end effector and pivotable about a second pivot axis defined between the middle joint housing and the distal joint housing, the second pivot axis being transverse to the first pivot axis.

19 Claims, 15 Drawing Sheets

Related U.S. Application Data division of application No. 14/075,180, filed on Nov. 8, 2013, now Pat. No. 9,295,522.

(51) Int. Cl.
  *F16H 35/00* (2006.01)
  *F16D 1/08* (2006.01)
  *A61B 34/30* (2016.01)

(52) U.S. Cl.
  CPC ...... *F16H 35/008* (2013.01); *A61B 2034/305* (2016.02); *Y10T 403/32008* (2015.01)

(56) References Cited

U.S. PATENT DOCUMENTS

| | | |
|---|---|---|
| 2,777,340 A | 1/1957 | Hettwer et al. |
| 2,957,353 A | 10/1960 | Babacz |
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,135 A | 8/1998 | Madhani et al. |
| 5,797,900 A | 8/1998 | Madhani et al. |
| 5,807,377 A | 9/1998 | Madhani et al. |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,976,122 A | 11/1999 | Madhani et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,364,888 B1 | 4/2002 | Niemeyer et al. |
| 6,368,324 B1 | 4/2002 | Dinger et al. |
| 6,371,909 B1 | 4/2002 | Hoeg et al. |
| 6,371,952 B1 | 4/2002 | Madhani et al. |
| 6,394,998 B1 | 5/2002 | Wallace et al. |
| 6,422,411 B1 | 7/2002 | Gray |
| 6,434,507 B1 | 8/2002 | Clayton et al. |
| 6,443,973 B1 | 9/2002 | Whitman |
| 6,460,718 B1 | 10/2002 | Vogel |
| 6,461,372 B1 | 10/2002 | Jensen et al. |
| 6,488,197 B1 | 12/2002 | Whitman |
| 6,491,201 B1 | 12/2002 | Whitman |
| 6,491,701 B2 | 12/2002 | Tierney et al. |
| 6,533,157 B1 | 3/2003 | Whitman |
| 6,537,280 B2 | 3/2003 | Dinger et al. |
| 6,554,844 B2 | 4/2003 | Lee et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,676,684 B1 | 1/2004 | Morley et al. |
| 6,685,698 B2 | 2/2004 | Morley et al. |
| 6,698,643 B2 | 3/2004 | Whitman |
| 6,699,177 B1 | 3/2004 | Wang et al. |
| 6,699,235 B2 | 3/2004 | Wallace et al. |
| 6,716,233 B1 | 4/2004 | Whitman |
| 6,743,240 B2 | 6/2004 | Smith et al. |
| 6,746,443 B1 | 6/2004 | Morley et al. |
| 6,783,533 B2 | 8/2004 | Green et al. |
| 6,786,896 B1 | 9/2004 | Madhani et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,817,974 B2 | 11/2004 | Cooper et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,866,671 B2 | 3/2005 | Tierney et al. |
| 6,902,560 B1 | 6/2005 | Morley et al. |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,066,926 B2 | 6/2006 | Wallace et al. |
| 7,077,856 B2 | 7/2006 | Whitman |
| 7,090,683 B2 | 8/2006 | Brock et al. |

(56) References Cited

U.S. PATENT DOCUMENTS

| | | |
|---|---|---|
| 7,111,769 B2 | 9/2006 | Wales et al. |
| 7,121,781 B2 | 10/2006 | Sanchez |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,169,141 B2 | 1/2007 | Brock et al. |
| 7,172,104 B2 | 2/2007 | Scirica et al. |
| 7,225,964 B2 | 6/2007 | Mastri et al. |
| 7,238,021 B1 | 7/2007 | Johnson |
| 7,241,288 B2 * | 7/2007 | Braun ............ A61B 17/29 606/1 |
| 7,246,734 B2 | 7/2007 | Shelton, IV |
| 7,297,142 B2 | 11/2007 | Brock |
| 7,316,681 B2 | 1/2008 | Madhani et al. |
| 7,320,700 B2 | 1/2008 | Cooper et al. |
| 7,328,828 B2 | 2/2008 | Ortiz et al. |
| 7,364,061 B2 | 4/2008 | Swayze et al. |
| 7,371,210 B2 | 5/2008 | Brock et al. |
| 7,380,695 B2 | 6/2008 | Doll et al. |
| 7,380,696 B2 | 6/2008 | Shelton, IV et al. |
| 7,398,707 B2 | 7/2008 | Morley et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,736,356 B2 | 6/2010 | Cooper et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,744,608 B2 | 6/2010 | Lee et al. |
| 7,744,622 B2 | 6/2010 | Brock et al. |
| 7,758,569 B2 | 7/2010 | Brock |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,775,972 B2 | 8/2010 | Brock et al. |
| 7,780,651 B2 | 8/2010 | Madhani et al. |
| 7,789,875 B2 | 9/2010 | Brock et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,819,884 B2 | 10/2010 | Lee et al. |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,854,738 B2 | 12/2010 | Lee et al. |
| 7,857,185 B2 | 12/2010 | Swayze et al. |
| 7,862,580 B2 | 1/2011 | Cooper et al. |
| 7,867,241 B2 | 1/2011 | Brock et al. |
| 7,870,989 B2 | 1/2011 | Viola et al. |
| 7,890,211 B2 | 2/2011 | Green |
| 7,905,828 B2 | 3/2011 | Brock et al. |
| 7,905,897 B2 | 3/2011 | Whitman et al. |
| 7,914,522 B2 | 3/2011 | Morley et al. |
| 7,918,230 B2 | 4/2011 | Whitman et al. |
| 7,918,861 B2 | 4/2011 | Brock et al. |
| 7,922,061 B2 | 4/2011 | Shelton, IV et al. |
| 7,922,719 B2 | 4/2011 | Ralph et al. |
| 7,942,868 B2 | 5/2011 | Cooper |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,004,229 B2 | 8/2011 | Nowlin et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,083,667 B2 | 12/2011 | Cooper et al. |
| 8,105,320 B2 | 1/2012 | Manzo |
| 8,114,118 B2 | 2/2012 | Knodel et al. |
| 8,123,740 B2 | 2/2012 | Madhani et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,160,743 B2 | 4/2012 | Birkenbach et al. |
| 8,182,470 B2 | 5/2012 | Devengenzo et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,282,653 B2 * | 10/2012 | Nelson ............ A61B 34/30 606/130 |
| 8,292,150 B2 | 10/2012 | Bryant |
| 8,292,888 B2 | 10/2012 | Whitman |
| 8,292,916 B2 | 10/2012 | Grace |
| 8,303,581 B2 | 11/2012 | Arts et al. |
| 8,337,521 B2 | 12/2012 | Cooper et al. |
| 8,342,379 B2 | 1/2013 | Whitman et al. |
| 8,343,141 B2 | 1/2013 | Madhani et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,398,634 B2 | 3/2013 | Manzo et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,758,391 B2 | 6/2014 | Swayze et al. |

(56) References Cited

U.S. PATENT DOCUMENTS

| Patent/Pub. No. | Date | Inventor |
|---|---|---|
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,028,468 B2 * | 5/2015 | Scarfogliero .......... A61B 34/30 606/1 |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 10,390,897 B2 * | 8/2019 | Kostrzewski ............. F16D 1/08 |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2005/0131442 A1 | 6/2005 | Yachia et al. |
| 2006/0027467 A1 | 2/2006 | Ferguson |
| 2006/0142656 A1 | 6/2006 | Malackowski et al. |
| 2006/0142740 A1 | 6/2006 | Sherman et al. |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0084898 A1 | 4/2007 | Scirica |
| 2007/0102472 A1 | 5/2007 | Shelton |
| 2007/0152014 A1 | 7/2007 | Gillum et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0118707 A1 | 5/2011 | Burbank |
| 2011/0118708 A1 | 5/2011 | Burbank et al. |
| 2011/0118709 A1 | 5/2011 | Burbank |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0209253 A1 | 8/2012 | Donhowe |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |

(56) References Cited

U.S. PATENT DOCUMENTS

| | | |
|---|---|---|
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 101856251 A | 10/2010 |
| CN | 102247182 A | 11/2011 |
| CN | 103379874 A | 10/2013 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1759652 A2 | 3/2007 |
| EP | 1769754 A1 | 4/2007 |
| EP | 1772105 A1 | 4/2007 |
| EP | 1813199 A1 | 8/2007 |
| EP | 1813203 A2 | 8/2007 |
| EP | 1813211 A2 | 8/2007 |
| EP | 1908412 A2 | 4/2008 |
| EP | 1917929 A1 | 5/2008 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 1952769 A2 | 8/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2090247 A1 | 8/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2245994 A1 | 11/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2377472 A1 | 10/2011 |
| EP | 2462878 A1 | 6/2012 |
| EP | 2462880 A2 | 6/2012 |
| EP | 2491872 A1 | 8/2012 |
| EP | 2586382 A2 | 5/2013 |
| EP | 2606834 A2 | 6/2013 |
| EP | 2668910 A2 | 12/2013 |
| EP | 2676615 A2 | 12/2013 |
| EP | 2815705 A1 | 12/2014 |
| ES | 2333509 A1 | 2/2010 |
| FR | 2861574 A1 | 5/2005 |
| JP | 08038488 | 2/1996 |
| JP | 2005125075 A | 5/2005 |
| KR | 20120022521 A | 3/2012 |
| WO | 9915086 A1 | 4/1999 |
| WO | 0072760 A1 | 12/2000 |
| WO | 0072765 A1 | 12/2000 |
| WO | 03000138 A2 | 1/2003 |
| WO | 03026511 A1 | 4/2003 |
| WO | 03030743 A2 | 4/2003 |
| WO | 03065916 A1 | 8/2003 |
| WO | 03077769 A1 | 9/2003 |
| WO | 03090630 A2 | 11/2003 |
| WO | 2004107989 A1 | 12/2004 |
| WO | 2004112618 A2 | 12/2004 |
| WO | 2006042210 A2 | 4/2006 |
| WO | 2007016290 A2 | 2/2007 |
| WO | 2007/026354 A1 | 3/2007 |
| WO | 2007137304 A2 | 11/2007 |
| WO | 2007146987 A2 | 12/2007 |
| WO | 2008131362 A2 | 10/2008 |
| WO | 2008133956 A2 | 11/2008 |
| WO | 2009039506 A1 | 3/2009 |
| WO | 2009039510 | 3/2009 |
| WO | 2007014355 A3 | 4/2009 |
| WO | 2009132359 A2 | 10/2009 |
| WO | 2009143092 A1 | 11/2009 |
| WO | 2009149234 A1 | 12/2009 |
| WO | 2011108840 A2 | 9/2011 |
| WO | 2012/040984 A1 | 4/2012 |

OTHER PUBLICATIONS

Extended European Search Report corresponding to International Application No. EP 15 17 3804.4 dated Nov. 24, 2015.

Extended European Search Report corresponding to International Application No. EP 15 18 8539.9 dated Feb. 17, 2016.

Extended European Search Report corresponding to International Application No. EP 15 17 3910.9 dated Nov. 13, 2015.

European Office Action corresponding to International Application No. EP 14 15 2236.7 dated Aug. 11, 2015.

Extended European Search Report corresponding to International Application No. EP 15 18 4915.5 dated Jan. 5, 2016.

Extended European Search Report for appln. No. 16178492.1 dated Oct. 14, 2016.

Australian Examination Report dated Jun. 21, 2018 issued in corresponding AU Appln. No. 2014227482.

Japanese Office Action dated Jul. 9, 2018 issued in corresponding JP Appln. No. 2014-216074.

Chinese Office Action dated Oct. 18, 2018 issued in corresponding CN Appln. No. 2014106439934.

Australian Examination Report dated Jul. 17, 2019 issued in corresponding AU Appln. No. 2018271364.

Extended European Search Report corresponding to International Application No. EP 15 15 1076.5 dated Apr. 22, 2015.

Japanese Office Action corresponding to International Application No. JP 2011-084092 dated Jan. 14, 2016.

Extended European Search Report corresponding to International Application No. EP 12 19 7970.2 dated Jan. 28, 2016.

Chinese Office Action corresponding to International Application No. CN 201210560638.1 dated Oct. 21, 2015.

European Office Action corresponding to International Application No. EP 14 15 9056.2 dated Oct. 26, 2015.

Australian Examination Report No. 1 corresponding to International Application No. AU 2015200153 dated Dec. 11, 2015.

Australian Examination Report No. 1 corresponding to International Application No. AU 2014204542 dated Jan. 7, 2016.

Chinese Office Action corresponding to International Application No. CN 201310125449.6 dated Feb. 3, 2016.

Extended European Search Report corresponding to International Application No. EP 15 19 0245.9 dated Jan. 28, 2016.

Extended European Search Report corresponding to International Application No. EP 15 16 7793.7 dated Apr. 5, 2016.

European Office Action corresponding to International Application No. EP 14 18 4882.0 dated Apr. 25, 2016.

Extended European Search Report corresponding to International Application No. EP 14 19 6704.2 dated Sep. 24, 2015.

International Search Report and Written Opinion corresponding to Int'l Appln. No. PCT/US2015/051837, dated Dec. 21, 2015.

Extended European Search Report corresponding to International Application No. EP 14 19 7563.1 dated Aug. 5, 2015.

(56) References Cited

OTHER PUBLICATIONS

Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to EP No. 13 16 3033.7, completed Jun. 27, 2013 and dated Jul. 15, 2013; (8 pp).
Extended European Search Report corresponding to EP No. 11 17 8021.9, dated Jun. 4, 2013; (3 pp).
Extended European Search Report corresponding to EP No. 12 18 6177.7, completed Aug. 14, 2013 and dated Aug. 23, 2013; (8 pp).
Partial European Search Report corresponding to EP No. 13 17 2400.7, completed Sep. 18, 2013 and dated Oct. 1, 2013; (7 pp).
Partial European Search Report corresponding to EP No. 13 17 1742.3, completed Sep. 17, 2013 and dated Sep. 25, 2013; (8 pp).
Extended European Search Report corresponding to EP No. 13 17 5475.6, completed Sep. 23, 2013 and dated Oct. 1, 2013; (8 pp).
Extended European Search Report corresponding to EP No. 13 17 5478.0, completed Sep. 24, 2013 and dated Oct. 2, 2013; (6 pp).
Extended European Search Report corresponding to EP No. 08 25 2703.7, completed Oct. 23, 2008 and dated Oct. 31, 2008; (7 pp).
International Search Report from the corresponding EP Application No. 12186177.7 dated Aug. 23, 2013.
International Search Report corresponding to PCT/US2005/027266, completed May 30, 2008 and dated Jun. 18, 2008; (2 pp.).
Extended European Search Report corresponding to EP 08 25 3184.9, completed Feb. 12, 2009 and dated Feb. 27, 2009; (3 pp.).
Extended European Search Report corresponding to EP 10 25 0228.3, completed May 20, 2010 and dated Jun. 1, 2010; (6 pp.).
Extended European Search Report corresponding to EP 10 25 2037.6, completed Mar. 1, 2011 and dated Mar. 9, 2011; (3 pp.).
Extended European Search Report corresponding to EP 10 25 1968.3, completed on Jul. 4, 2011 and dated Jul. 14, 2011; (12 pp.).
Extended European Search Report corresponding to EP 11 15 2266.0, completed Jul. 15, 2011 and dated Jul. 28, 2011; (3 pp.).
Extended European Search Report corresponding to EP 11 25 0462.6, completed Jul. 20, 2011 and dated Jul. 28, 2011; (6 pp.).
Extended European Search Report corresponding to EP 11 25 0771.0, completed Feb. 7, 2012 and dated Feb. 17, 2012; (3 pp.).
Extended European Search Report corresponding to EP 06 78 8914.7, completed May 3, 2012 and dated May 11, 2012; (8 pp.).
Partial European Search Report corresponding to EP 12 18 6177.7, completed Jan. 30, 2013 and dated Feb. 12, 2013; (6 pp.).
Extended European Search Report corresponding to EP 08 25 2703.7, completed Oct. 23, 2008 and dated Oct. 31, 2008; (7 pp.).
Extended European Search Report corresponding to EP No. 13 17 5479.8, completed Sep. 27, 2013 and dated Oct. 10, 2013; (7 pp).
Partial Extended European Search Report corresponding to EP 13 17 5477.2, completed Oct. 7, 2013 and dated Oct. 15, 2013; (7 pp).
European search Report from Appl. No. 13177163.6 dated Nov. 15, 2013. (8 pp).
Extended European Search Report from EP Application No. 13172400.7 dated Jan. 21, 2014.
Extended European Search Report from EP Application No. 13189026.1 dated Jan. 31, 2014.
The extended European Search Report from Application No. EP 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805.3, dated Nov. 4, 2013.
Extended European Search Report from Application No. EP 13171742.3 dated Jan. 3, 2014.
European Search Report No. 14192217.9 dated Feb. 5, 2015.
Canadian Office Action dated Aug. 28, 2020 issued in corresponding CA Appln. No. 2,865,105.
Extended European Search Report from Application No. EP 13177163.6 dated Feb. 6, 2014.
Chinese Office Action dated Feb. 2, 2018 issued in corresponding Chinese Application No. 2014106439934.

\* cited by examiner

MEDICAL DEVICE ADAPTER WITH WRIST MECHANISM

CROSS-REFERENCE TO RELATED APPLICATIONS

This application is a continuation of U.S. patent application Ser. No. 15/049,651, filed on Feb. 22, 2016, which is a divisional of U.S. patent application Ser. No. 14/075,180, filed on Nov. 8, 2013, now U.S. Pat. No. 9,295,522, the entire disclosure of each of which is incorporated by reference herein.

TECHNICAL FIELD

The present disclosure relates to surgical apparatuses, devices and/or systems for performing endoscopic surgical procedures and methods of use thereof. More specifically, the present disclosure relates to electromechanical adapters, devices and/or systems configured for use with handheld or robotic surgical apparatuses and removable disposable loading units and/or single use loading units for clamping, cutting and/or stapling tissue.

BACKGROUND

Currently there are various drive systems for operating and/or manipulating electromechanical surgical devices. In many instances the electromechanical surgical devices include a reusable actuation assembly (e.g., motorized or manual tool handle or robotic), and disposable or single-use loading units. The loading units are selectively connected to the actuation assembly prior to use and then disconnected from the actuation assembly following use in order to be disposed of or in some instances sterilized for re-use.

Many of the existing end effectors for use with the existing surgical devices and/or actuation assemblies are driven by a linear force, such as end effectors for performing endo-gastrointestinal anastomosis procedures, end-to-end anastomosis procedures, and transverse anastomosis procedures. As such, these end effectors are not compatible with surgical devices and/or actuation assemblies that use rotary motion to deliver power or the like.

In order to make the linear driven end effectors compatible with surgical devices and/or actuation assemblies that use a rotary motion to deliver power, a need exists for adapters and/or adapter assemblies to interface between and interconnect the linear driven end effectors with the rotary driven surgical devices and/or handle assemblies.

SUMMARY

Further details and aspects of exemplary embodiments of the present invention are described in more detail below with reference to the appended Figures.

According to one embodiment of the present disclosure, a surgical device adapter for coupling an end effector to a surgical device is disclosed. The surgical device adapter includes: a proximal joint housing including a proximal end and a distal end, the proximal joint housing coupleable at the proximal end thereof to the surgical device; a middle joint housing having a proximal end and a distal end, the middle joint housing pivotally coupled at the proximal end thereof to the distal end of the proximal joint housing, the middle joint housing pivotable about a first pivot axis defined between the proximal joint housing and the middle joint housing; and a distal joint housing having a proximal end and a distal end, the distal join housing pivotally coupled at the proximal end thereof to the distal end of the middle joint housing, the distal joint housing coupleable at the distal end thereof to the end effector and pivotable about a second pivot axis defined between the middle joint housing and the distal joint housing, the second pivot axis being transverse to the first pivot axis.

According to one aspect of the above embodiment, the surgical device is a handheld surgical device or a robotic surgical device.

According to another aspect of the above embodiment, the adapter further includes: a first articulation link coupled to the middle joint housing, the first articulation link longitudinally movable in a proximal direction to pivot the middle joint housing in a first direction about the first pivot axis and in a distal direction to pivot the middle joint housing in a second direction about the first pivot axis.

The adapter may further include: a second articulation link coupled to the distal joint housing, the second articulation link longitudinally movable in a proximal direction to pivot the distal joint housing in a first direction about the second pivot axis and in a distal direction to pivot the distal joint housing in a second direction about the second pivot axis.

According to one aspect of the above embodiment, the second articulation link is bendable in response to pivoting of the middle joint housing.

According to another aspect of the above embodiment, the adapter further includes: a drive mechanism couplable to the surgical device and the end effector, the drive mechanism configured to actuate the end effector in response to input from the surgical device.

The drive mechanism may also include: a proximal transmission shaft rotatably disposed within the proximal joint housing, the proximal transmission shaft including a connector sleeve disposed at a proximal end thereof couplable to the surgical device and a first gear disposed at a distal end thereof; a middle transmission shaft rotatably disposed within the middle joint housing, the middle transmission shaft including a second gear disposed at a proximal end thereof and meshingly engaged with the first gear and a third gear disposed at a distal end thereof; and a distal transmission shaft rotatably disposed within the distal joint housing, the distal transmission shaft including a fourth gear disposed at a proximal end thereof and meshingly engaged with the third gear and a keyed distal end configured to engage the end effector. The first, second, third, and fourth gears have a substantially ellipsoid shape.

According to another embodiment of the present disclosure, a surgical device adapter for coupling an end effector to a surgical device is disclosed. The surgical device adapter includes: a proximal joint housing including a proximal end and a distal end, the proximal joint housing couplable at the proximal end thereof to the surgical device; a middle joint housing having a proximal end and a distal end, the middle joint housing pivotally coupled at the proximal end thereof to the distal end of the proximal joint housing, the middle joint housing pivotable about a first pivot axis defined between the proximal joint housing and the middle joint housing; and a distal joint housing having a proximal end and a distal end, the distal join housing pivotally coupled at the proximal end thereof to the distal end of the middle joint housing, the distal joint housing coupleable at the distal end thereof to the end effector and pivotable about a second pivot axis defined between the middle joint housing and the distal joint housing, the second pivot axis being transverse to the first pivot axis; and a drive mechanism including a plurality of gears and couplable to the surgical device and the end effector, the drive mechanism configured to actuate the end effector in response to input from the surgical device, wherein the plurality of gears are disposed between the proximal, middle, and distal joint housings.

According to one aspect of the above embodiment, the surgical device is a handheld surgical device or a robotic surgical device.

According to another aspect of the above embodiment, the adapter further includes: a first articulation link coupled to the middle joint housing, the first articulation link longitudinally movable in a proximal direction to pivot the middle joint housing in a first direction about the first pivot axis and in a distal direction to pivot the middle joint housing in a second direction about the first pivot axis.

The adapter may further include: a second articulation link coupled to the distal joint housing, the second articulation link longitudinally movable in a proximal direction to pivot the distal joint housing in a first direction about the second pivot axis and in a distal direction to pivot the distal joint housing in a second direction about the second pivot axis.

According to one aspect of the above embodiment, the second articulation link is bendable in response to pivoting of the middle joint housing.

According to another aspect of the above embodiment, the drive mechanism includes: a proximal transmission shaft rotatably disposed within the proximal joint housing, the proximal transmission shaft including a connector sleeve disposed at a proximal end thereof couplable to the surgical device and a first gear disposed at a distal end thereof.

The drive mechanism may also include: a middle transmission shaft rotatably disposed within the middle joint housing, the middle transmission shaft including a second gear disposed at a proximal end thereof and meshingly engaged with the first gear and a third gear disposed at a distal end thereof.

According to one aspect of the above embodiment, the drive mechanism includes: a distal transmission shaft rotatably disposed within the distal joint housing, the distal transmission shaft including a fourth gear disposed at a proximal end thereof and meshingly engaged with the third gear and a keyed distal end configured to engage the end effector.

According to another aspect of the above embodiment, the first, second, third, and fourth gears have a substantially ellipsoid shape.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1A:
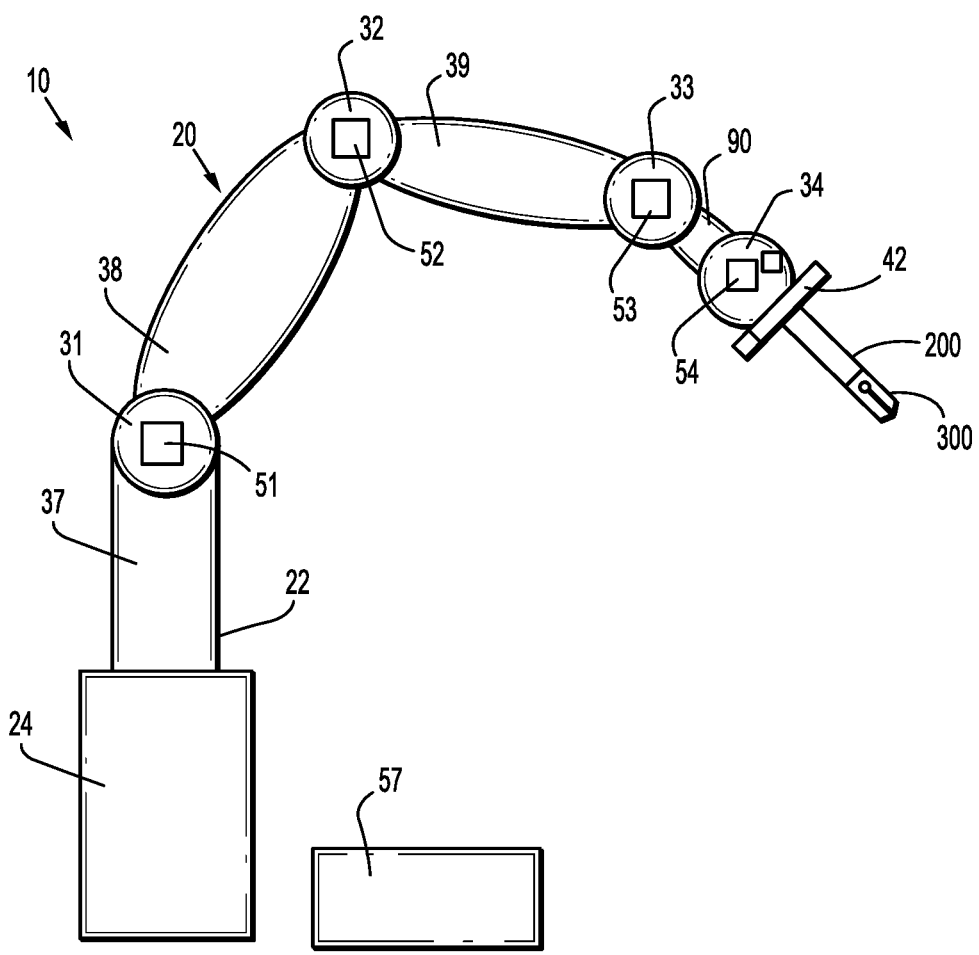
FIG. 1A is a schematic illustration of an electromechanical surgical system including a robotic actuation assembly, an end effector and an adapter assembly according to the present disclosure.

Embodiments of the presently disclosed electromechanical surgical system, apparatus and/or device are described in detail with reference to the drawings, in which like reference numerals designate identical or corresponding elements in each of the several views. As used herein the term "distal" refers to that portion of the electromechanical surgical system, apparatus and/or device, or component thereof, that are farther from the user, while the term "proximal" refers to that portion of the electromechanical surgical system, apparatus and/or device, or component thereof, that are closer to the user. The terms "left" and "right" refer to that portion of the electromechanical surgical system, apparatus and/or device, or component thereof, that are on the left and right sides, respectively, from the perspective of the user facing the distal end of the electromechanical surgical system, apparatus and/or device from the proximal end while the surgical system, apparatus and/or device is oriented in non-rotational (e.g., home) configuration.

With reference to FIG. 1A, an embodiment of the electrosurgical powered surgical system 10 is shown. Electromechanical surgical system 10 includes a surgical apparatus or device in the form of a robotic surgical apparatus 20 that is configured for selective attachment thereto of a plurality of different end effectors 300, via a first adapter assembly 200 (e.g., elongated body).

The robotic surgical apparatus 20 includes a robot arm 22 coupled to a base 24. Robot arm 22 may include a plurality of limbs or levers 37-40 interconnected to one another by a plurality of elbows or axes 31-34, and a flange 42 supported on a distal-most axis 34, to which the end effector 300 is attached through the first adapter assembly 200.

In the case of the present exemplary embodiment, each of the axes 31-34 is moved by an electric drive 51-54, respectively, each of which is electrically connected to a controller 57 of robotic surgical apparatus 20, so that controller 57, or a computer readable set of instructions running on controller 57, is able to actuate electric drives 51-56 in such a way that the position and orientation of flange 42 of robotic surgical apparatus 20 can be set essentially freely in space. Each of the electric drives 51-54 of robotic surgical apparatus 20 includes an electric motor and any power-generating or control electronics that actuate the motors.

Robotic surgical apparatus 20 may also be configured to work with robotic surgical systems. Such systems employ various robotic elements (e.g., robotic surgical apparatus 20) to assist the surgeon in the operating theater and allow remote operation or partial remote operation of surgical instrumentation (e.g., end effector 300). Various robotic arms, gears, cams, pulleys, electric and mechanical motors, etc. of the robotic surgical apparatus 20 may be employed for this purpose and may be designed to assist the surgeon during the course of an operation or treatment. Robotic surgical apparatus 20 may include, remotely steerable systems, automatically flexible surgical systems, remotely flexible surgical systems, remotely articulating surgical systems, wireless surgical systems, modular or selectively configurable remotely operated surgical systems, and combinations thereof.

The robotic surgical apparatus 20 may be employed with one or more consoles that are next to the operating theater or located in a remote location. In embodiments, one team of surgeons or nurses may prep the patient for surgery and configure the robotic surgical apparatus 20 with one or more of the end effectors 300 disclosed herein while another surgeon or group of surgeons remotely control the end effector 300 via the robotic surgical apparatus 20. As can be appreciated, a highly skilled surgeon may perform multiple operations in multiple locations without leaving his/her remote console, which can be both economically advantageous and a benefit to the patient or a series of patients.

The robotic surgical apparatus 20 of the surgical system may be coupled to one or more master handles (not shown) coupled locally or remotely to the controller 57. The handles may be moved by the surgeon to produce a corresponding movement of the working ends of any type of surgical instrument (e.g., end effectors 300, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the surgeon can control the resolution of the working ends of the surgical instrument(s).

The master handles may include various sensors to provide feedback (e.g., haptic) to the surgeon relating to various tissue parameters or conditions, e.g., resistance due to manipulation, cutting or otherwise treating tissue, pressure by the instrument onto the tissue, tissue temperature, tissue impedance, and combinations thereof. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 1B:
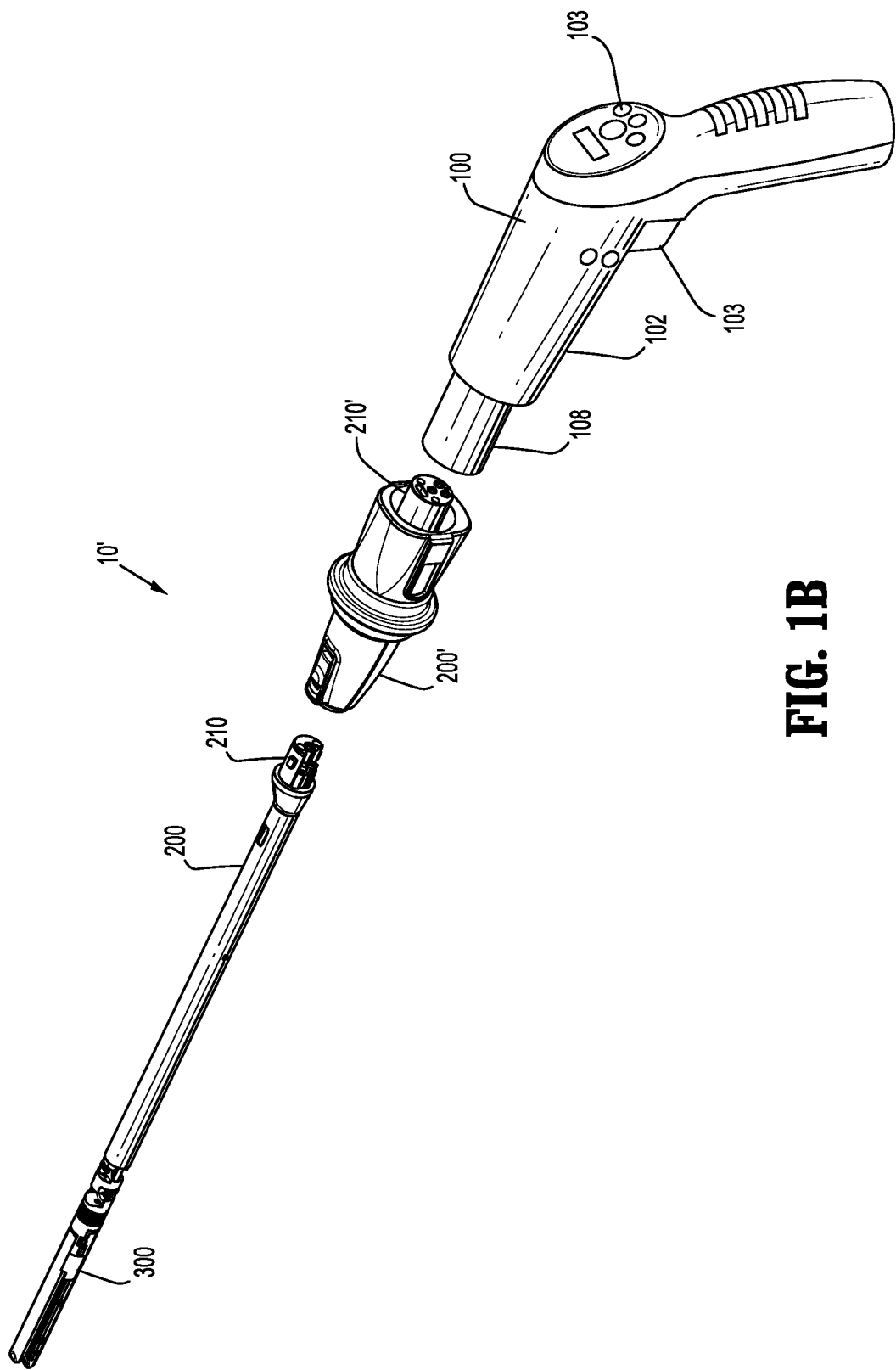
FIG. 1B is a perspective view of an electromechanical surgical system including a handheld actuation assembly according to the present disclosure and the end effector and the adapter assembly of FIG. 1A.

Referring to FIG. 1B, another embodiment of the electromechanical powered surgical system 10' is shown. Electromechanical surgical system 10' includes a surgical apparatus or device in the form of an electromechanical, hand-held, powered surgical instrument 100 that is configured for selective attachment thereto of a plurality of different end effectors 300, via the first adapter assembly 200 (e.g., elongated body). A secondary adapter assembly 200' may also be utilized to mate the first adapter assembly 200, which is used to couple to the robotic surgical apparatus 20, to the powered surgical instrument 100. The end effector 300 and the adapter assemblies 200 and 200' are configured for actuation and manipulation by the surgical instrument 100. In particular, the surgical instrument 100, the adapter assemblies 200 and 200', and the end effector 300 are separable from each other such that the surgical instrument 100 is configured for selective connection with first adapter assembly 200 via the secondary adapter assembly 200', and, in turn, first adapter assembly 200 is configured for selective connection with any one of a plurality of different end effectors 300. In embodiments, the surgical instrument 100 may be operated directly with the first adapter assembly 200.

Reference may be made to International Application No. PCT/US2008/077249, filed Sep. 22, 2008 (Inter. Pub. No. WO 2009/039506), and U.S. Patent Application Publication No. 2011/0121049, published May 26, 2011, the entire contents of all of which are incorporated herein by reference, for a detailed description of the construction and operation of exemplary electromechanical, hand-held, powered surgical instruments 100.

With reference to FIG. 1B, surgical instrument 100 includes a handle housing 102 including one or more controllers, a power source, and a drive mechanism having one or more motors, gear selector boxes, gearing mechanisms, and the like. The housing 102 also supports a control assembly 103. Control assembly 103 may include one or more finger-actuated control buttons, rocker devices, joystick or other directional controls, whose input is transferred to the drive mechanism to actuate the first adapter assembly 200 and the end effector 300.

Figure 4:
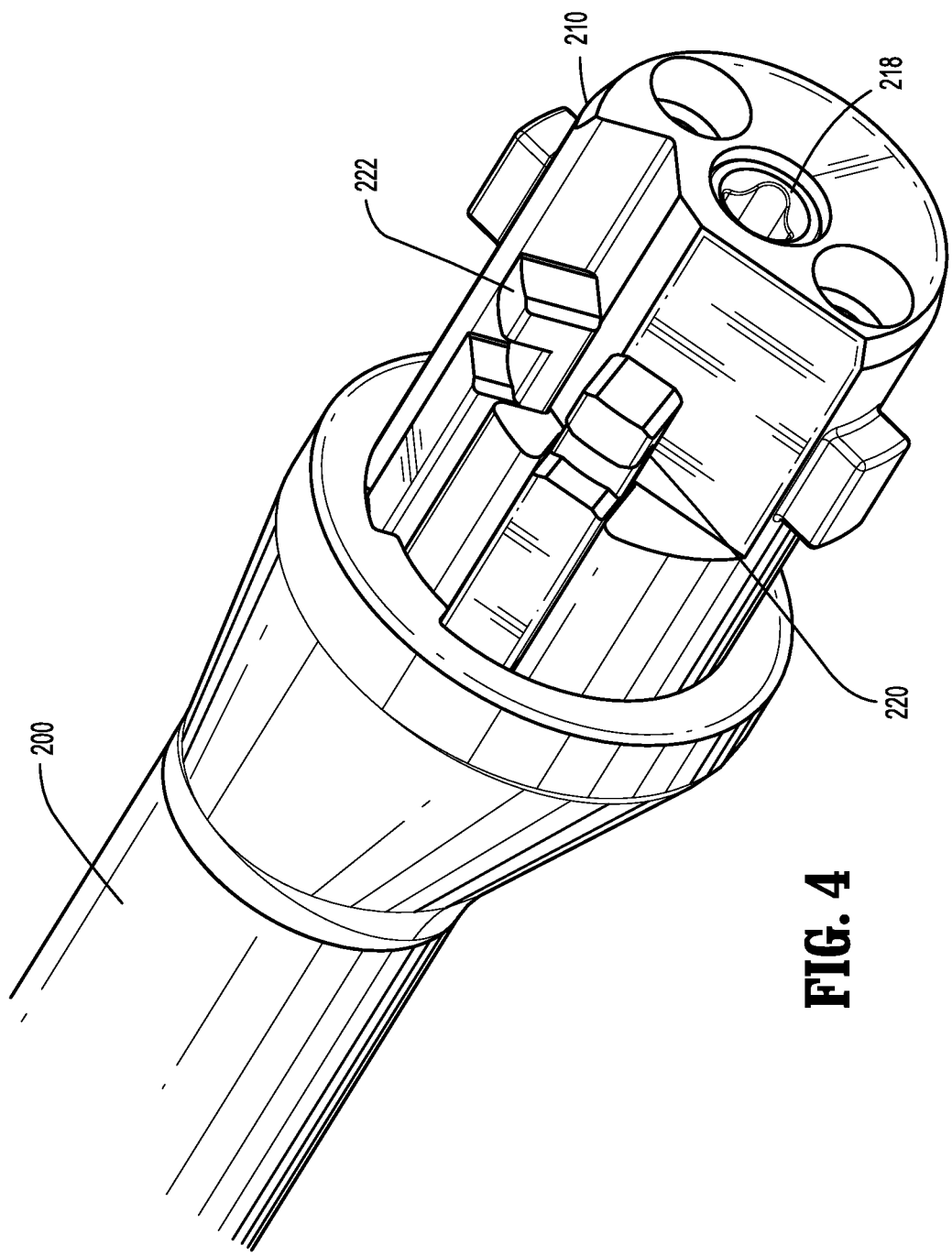
FIG. 4 is a perspective, enlarged view of a proximal end of the adapter assembly of FIG. 1A according to the present disclosure.
Figure 5:
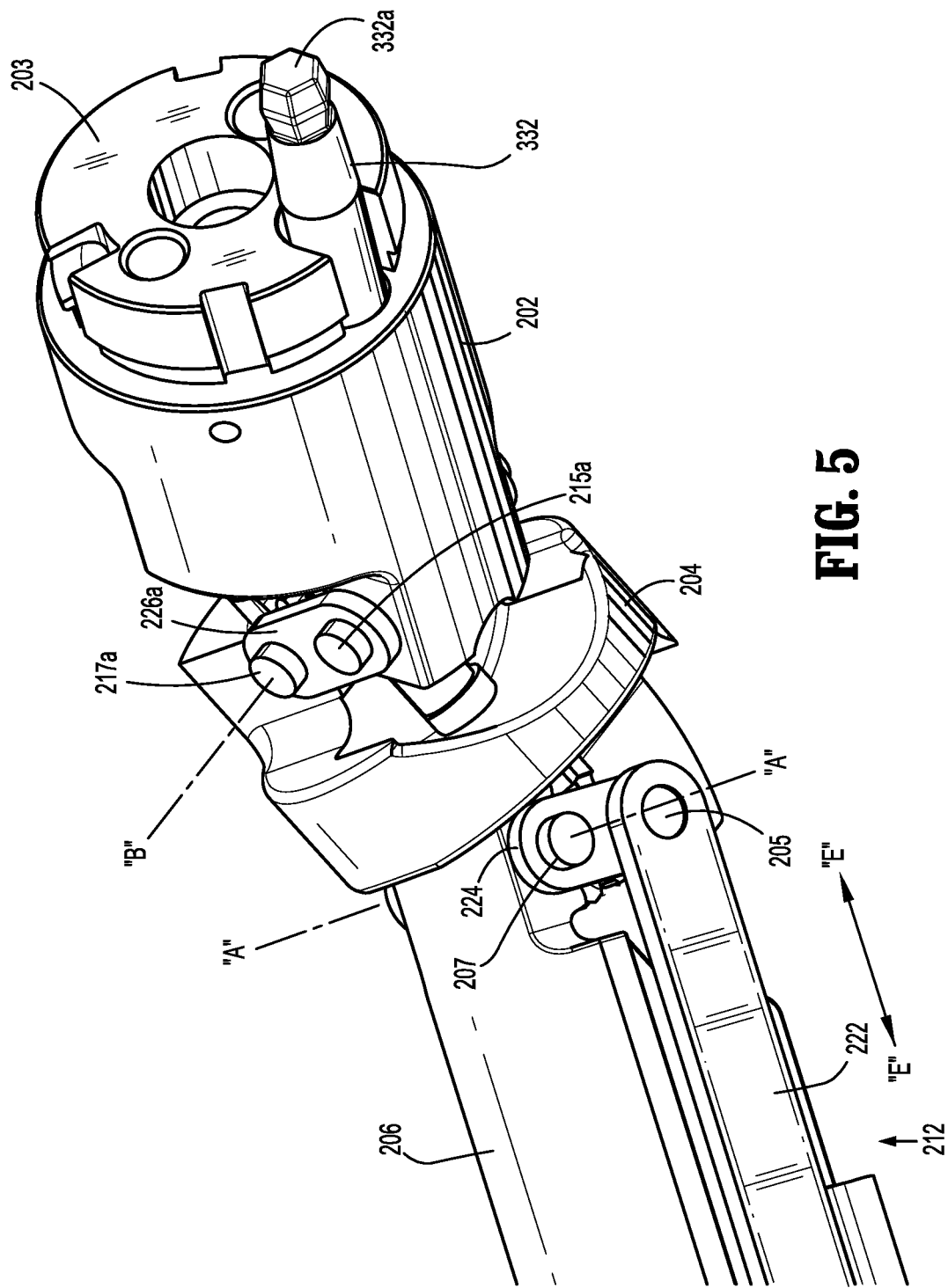
FIG. 5 is a perspective, partially-disassembled view of the distal end of the adapter assembly of FIG. 1A with a proximal articulation mechanism according to the present disclosure.

The housing 102 defines a nose or connecting portion 108 configured to accept a corresponding drive coupling assembly 210' of secondary adapter assembly 200' (FIG. 5). Connecting portion 108 houses one or more rotatable drive connectors that interface with corresponding rotatable connector sleeves (not shown) of the first adapter assembly 200'. The secondary adapter assembly 200' is configured to accept a corresponding drive coupling assembly 210 of first adapter assembly 200. The adapter assembly 200' and the robotic surgical apparatus 20 include one or more rotatable and/or longitudinally movable drive connectors that interface with corresponding rotatable connector sleeve 218 (FIGS. 2 and 4) and longitudinally movable first and second articulation links 220 and 222 (FIGS. 2 and 4) of the first adapter assembly 200, as described in further detail below.

Figure 2:
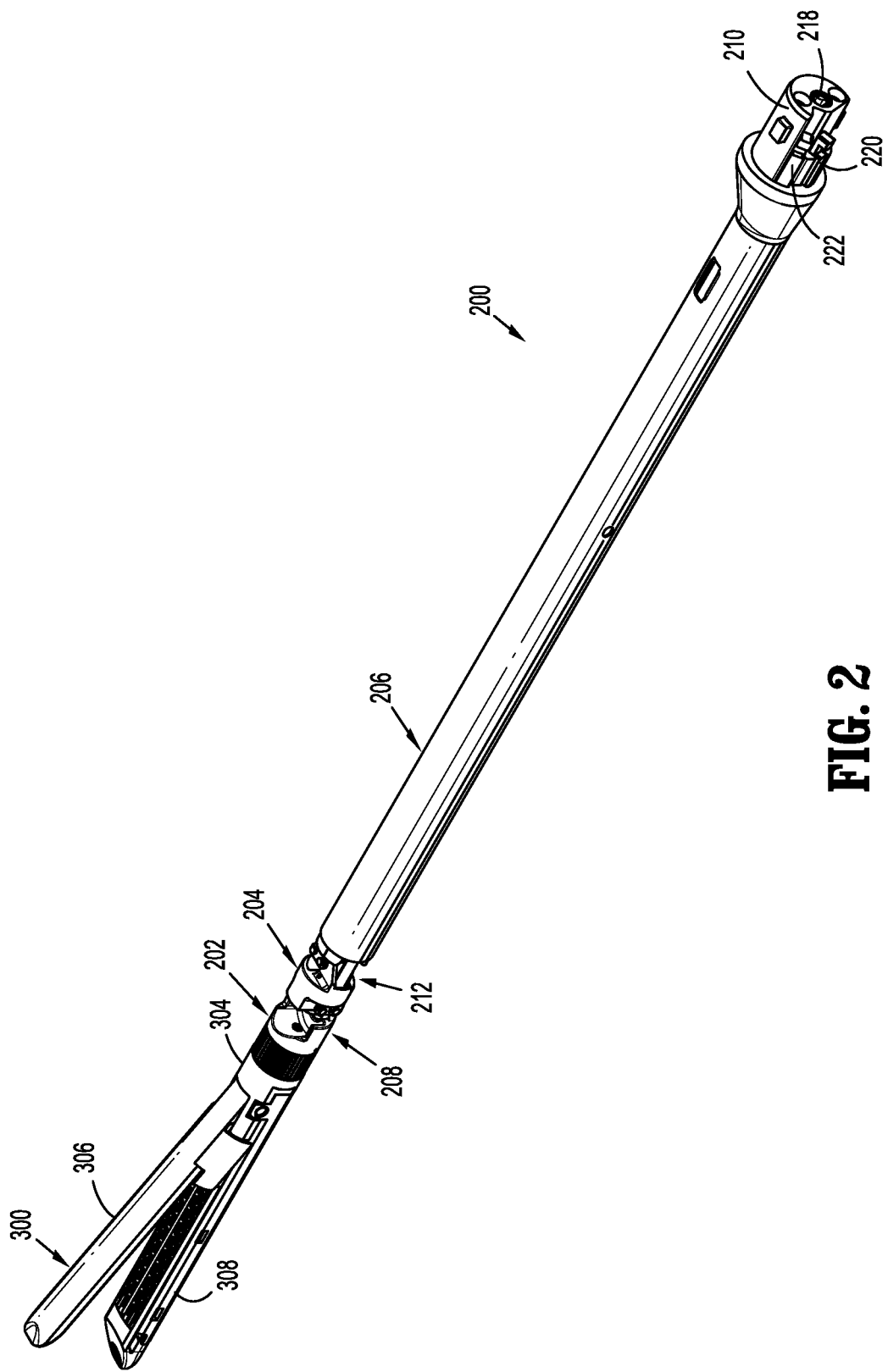
FIG. 2 is a perspective view of the adapter assembly with the end effector of FIG. 1A in an unarticulated configuration according to the present disclosure.
Figure 3:
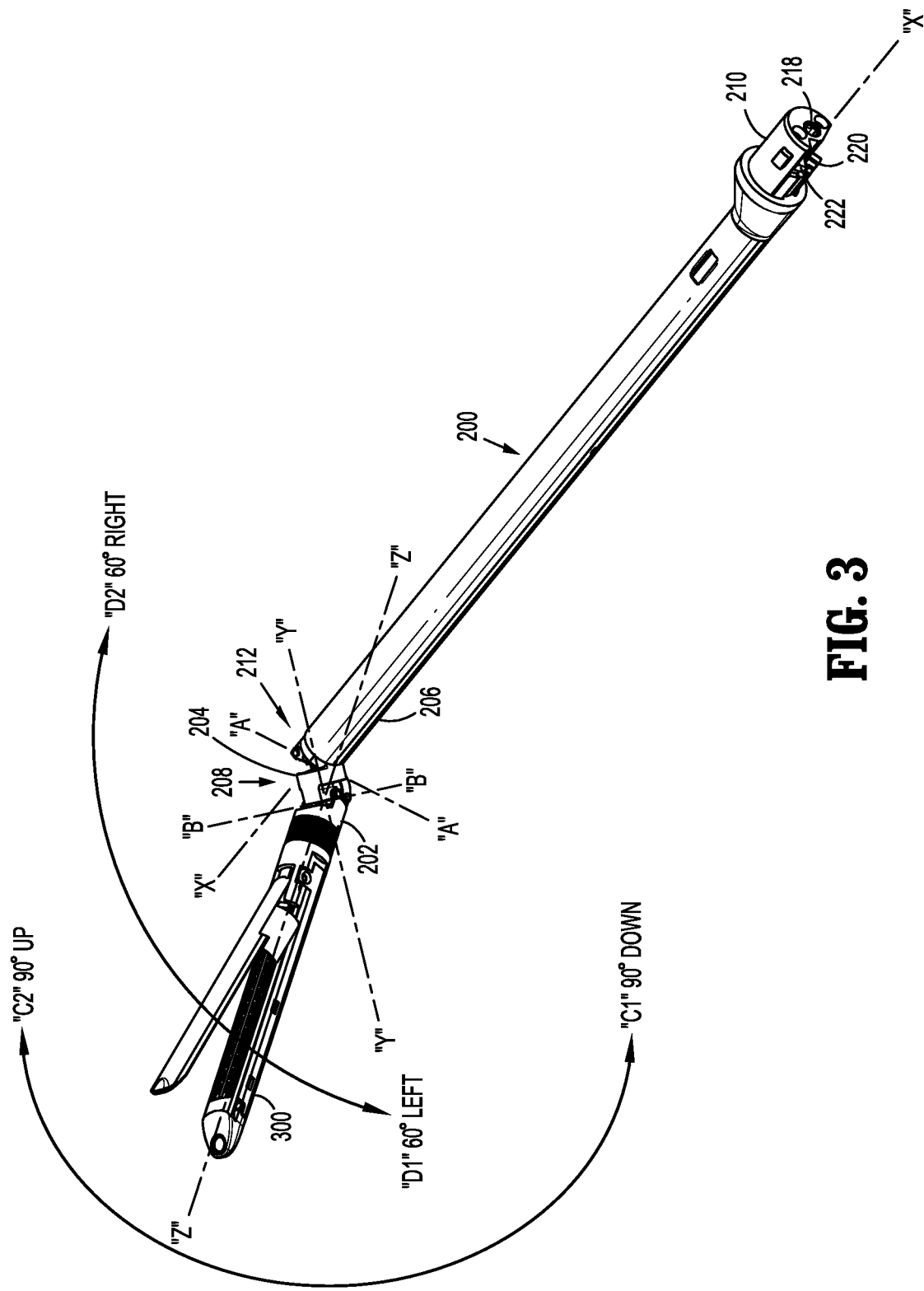
FIG. 3 is a perspective view of the adapter assembly with the end effector of FIG. 1A in an articulated configuration according to the present disclosure.

With reference to FIG. 2, the first adapter assembly 200 is shown in an unarticulated configuration. The first adapter assembly 200 includes a distal joint housing 202 configured to couple to the end effector 300. The distal joint housing 202 is pivotally coupled to a middle joint housing 204, which in turn, is pivotally coupled to a proximal joint housing 206. With reference to FIG. 3, the middle joint housing 204 is independently pivotable relative to proximal joint housing 206 by a proximal articulation assembly 212. The distal joint housing 202 is pivotable relative to the middle joint housing 204 by a distal articulation assembly 208.

When first adapter assembly 200 is mated to secondary adapter assembly 200' (FIG. 1B), or to the robotic surgical apparatus 20, the drive connectors (not shown) of second adapter assembly 200', or of the robotic surgical apparatus 20, couple with the rotatable connector sleeves 218 (FIGS. 2 and 4) and articulation links 220 and 222 of first adapter assembly 200 (FIGS. 2 and 4). In this regard, the interface between drive connectors (not shown) and connector sleeve 218 and articulation links 220 and 222 are keyed such that rotation and/or movement of each of drive connectors of secondary adapter assembly 200', or the robotic surgical apparatus 20, causes a corresponding rotation and/or movement of the corresponding connector sleeve 218 and articulation links 220 and 222 of first adapter assembly 200. This allows for longitudinal and/or rotational forces to be independently transmitted via each of the three respective connector interfaces.

The drive mechanisms of the surgical instrument 100 and the robotic surgical apparatus 20 are configured to drive shafts and/or gear components in order to selectively move tool assembly 304 of end effector 300 relative to proximal body portion 302 of end effector 300, to rotate end effector 300 relative to first adapter assembly 200 about a longitudinal axis "X-X" (FIG. 3) defined by the first adapter assembly 200, actuate various components of the tool assembly 304, e.g., to move anvil assembly 306 relative to cartridge assembly 308 of end effector 300, and/or to fire a stapling and cutting cartridge within cartridge assembly 308 of end effector 300 (FIG. 2).

The selective rotation and/or movement of drive connector(s) of surgical instrument 100 and/or robotic surgical apparatus 20 allows surgical instrument 100 and/or robotic surgical apparatus 20 to selectively actuate different functions of end effector 300. As discussed in greater detail below, selective and independent rotation of connector sleeve 218 of first adapter assembly 200 corresponds to the selective and independent opening and closing of tool assembly 304 of end effector 300, and driving of a stapling/cutting component of tool assembly 304 of end effector 300. In embodiments, rotation of the connector sleeve 218 may be used to rotate end effector 300 relative to first adapter assembly 200 about the longitudinal axis "X-X."

With reference to FIGS. 2 and 3, selective and independent movement of articulation links 220 and 222 corresponds to the selective and independent actuation of the distal and proximal articulation assemblies 208 and 212, respectively. More specifically, as shown in FIG. 3, the middle joint housing 204 is pivotable relative to the proximal joint housing 206 about a pivot axis "A-A" in directions "C1" or "C2." The middle joint housing 204 may be pivoted from an unarticulated configuration in which the longitudinal axes "X-X" and "Y-Y" defined by the proximal and middle joint housings 206 and 204, respectively, are aligned (e.g. zero angle) as shown in FIG. 2 to an articulated configuration in which the longitudinal axes "X-X" and "Y-Y" are in non-parallel alignment (e.g., non-zero angle) as shown in FIG. 3. The middle joint housing 204 may be articulated about the pivot axis "A-A" from about 5° to about 170°, in embodiments, about 60°.

The distal joint housing 202 is pivotable relative to the middle joint housing 204 about a pivot axis "B-B" in directions "D1" or "D2." The distal joint housing 202 may be pivoted from an unarticulated configuration in which the longitudinal axes "Y-Y" and "Z-Z" defined by the middle and distal joint housings 204 and 202, respectively, are aligned (e.g. zero angle) as shown in FIG. 2 to an articulated configuration in which the longitudinal axes "Y-Y" and "Z-Z" are in non-parallel alignment (e.g., non-zero angle) as shown in FIG. 3. The distal joint housing 202 may be articulated about the pivot axis "B-B" from about 5° to about 170°, in embodiments about 90°. The pivot axes "A-A" and "B-B" are transverse relative to each other allowing for two-dimensional articulation of the end effector 300 relative to the proximal joint housing 206.

With reference to FIGS. 5-9, proximal articulation assembly 212 for pivoting middle joint housing 204 relative to proximal joint housing 206 is shown. The proximal articulation assembly 212 includes the second articulation link 222 longitudinally movable within the proximal joint housing 206. The proximal joint housing 206 is pivotally coupled to the middle joint housing 204 via a lever 224. The lever 224 is pivotally coupled at one end to a pivot pin 207 disposed at a distal end of the proximal joint housing 206 and at another end to a pivot pin 205 disposed at a proximal end of the middle joint housing 204.

Figure 6:
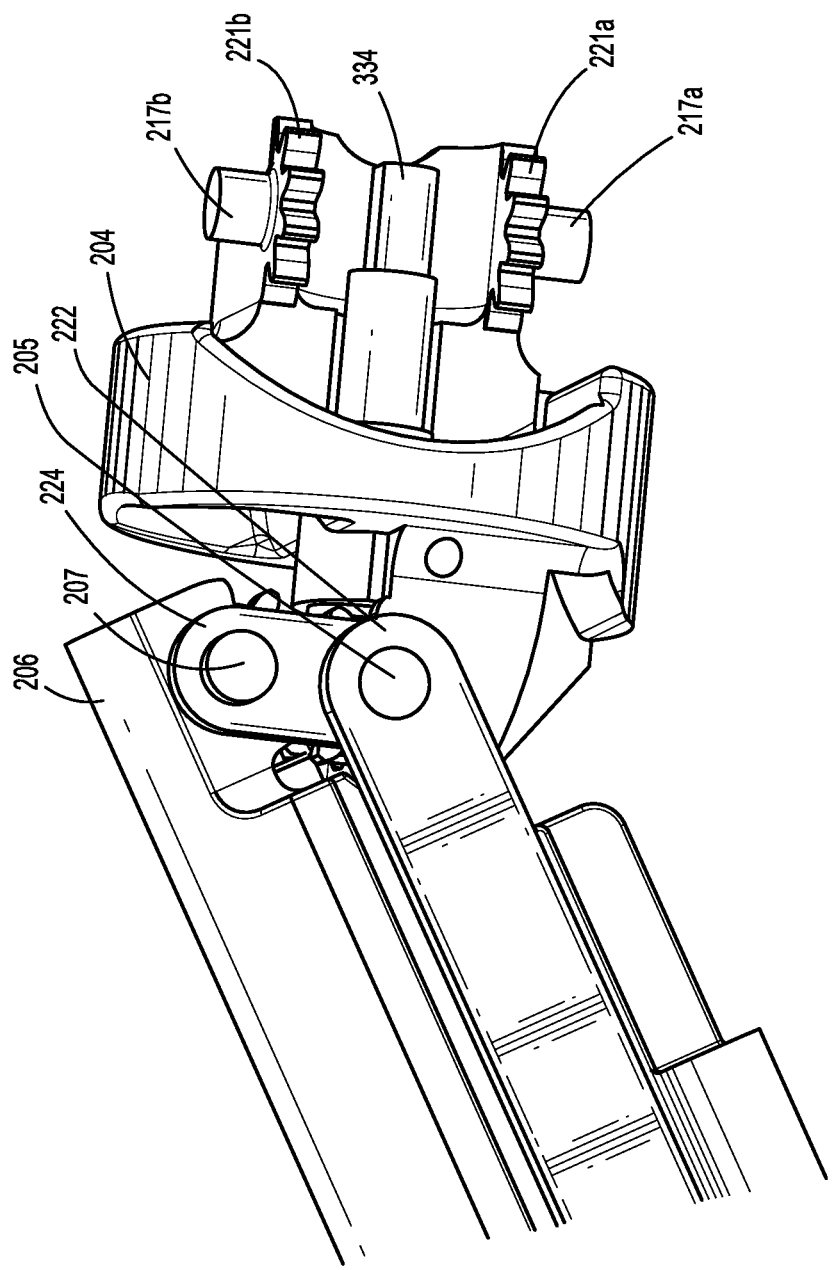
FIG. 6 is a perspective, partially-disassembled view of the proximal end of the adapter assembly of FIG. 1A with the proximal articulation mechanism in a first configuration according to the present disclosure.
Figure 7:
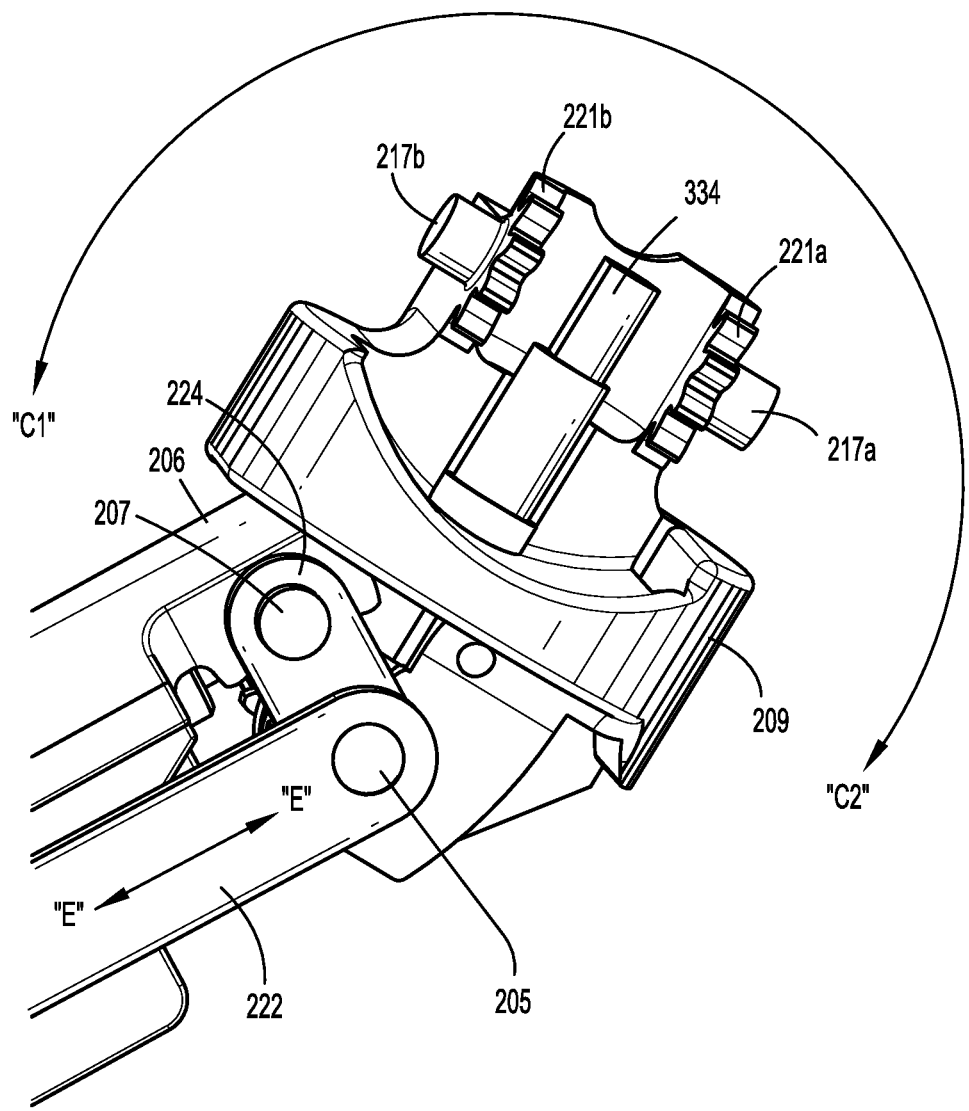
FIG. 7 is a perspective, partially-disassembled view of the proximal end of the adapter assembly of FIG. 1A with the proximal articulation mechanism in a second configuration according to the present disclosure.

The second articulation link 222 is also pivotally coupled to the pivot pin 205. The pivot pin 207 defines the pivot axis "A-A" and acts as a fulcrum for the lever 224, which pivots about the pivot pin 207 as the second articulation link 222 is moved along a longitudinal direction "E" (FIG. 5). In particular, as the second articulation link 222 is moved in the proximal direction, as shown in FIGS. 5 and 7, the middle joint housing 204 is pivoted about the pivot pin 205 along with the lever 224 which is pivoted about the pivot pin 207 in a counterclockwise direction "C1" (FIG. 3). Distal movement of the second articulation link 222, as shown in FIG. 6, reverses pivoting of the middle joint housing 204 in a clockwise direction "C2."

Figure 8:
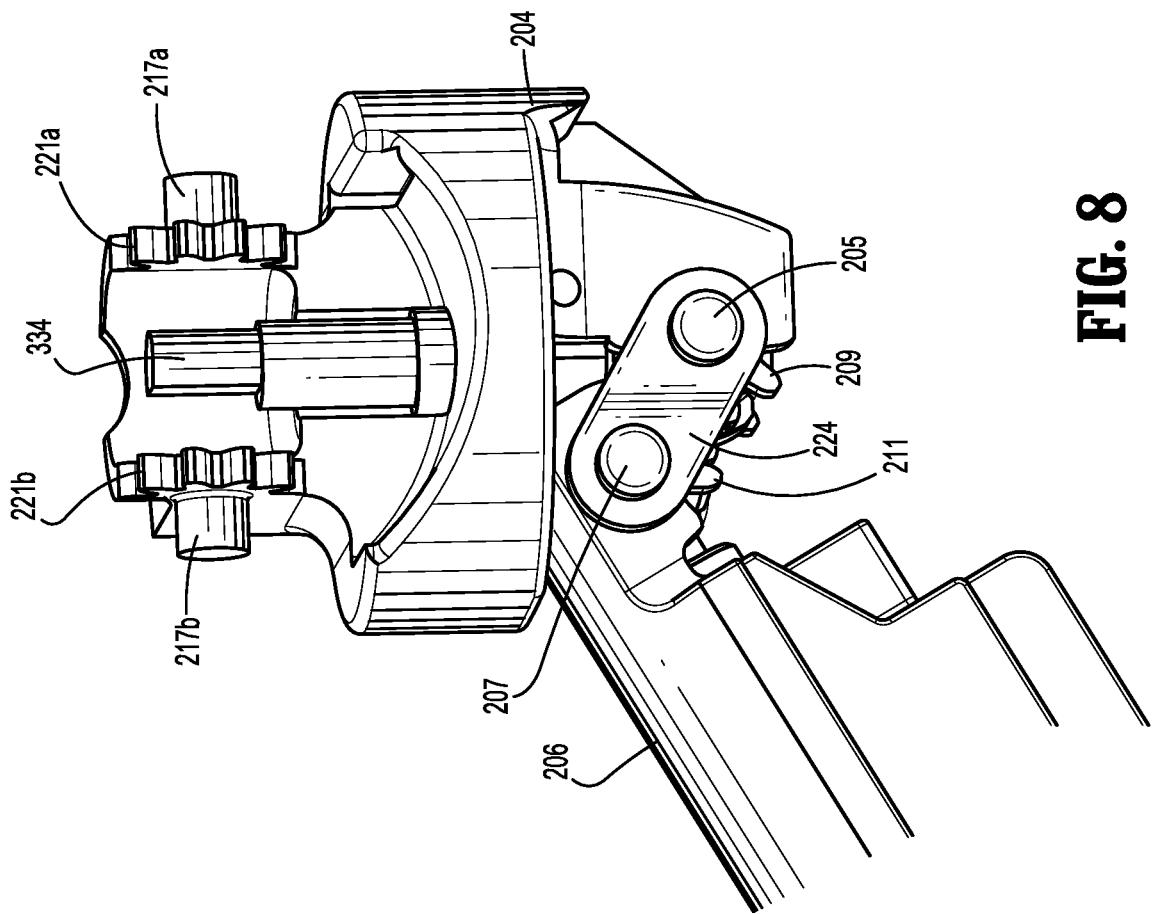
FIG. 8 is a further perspective, partially-disassembled view of the proximal end of the adapter assembly of FIG. 1A with the proximal articulation mechanism in the second configuration according to the present disclosure.
Figure 9:
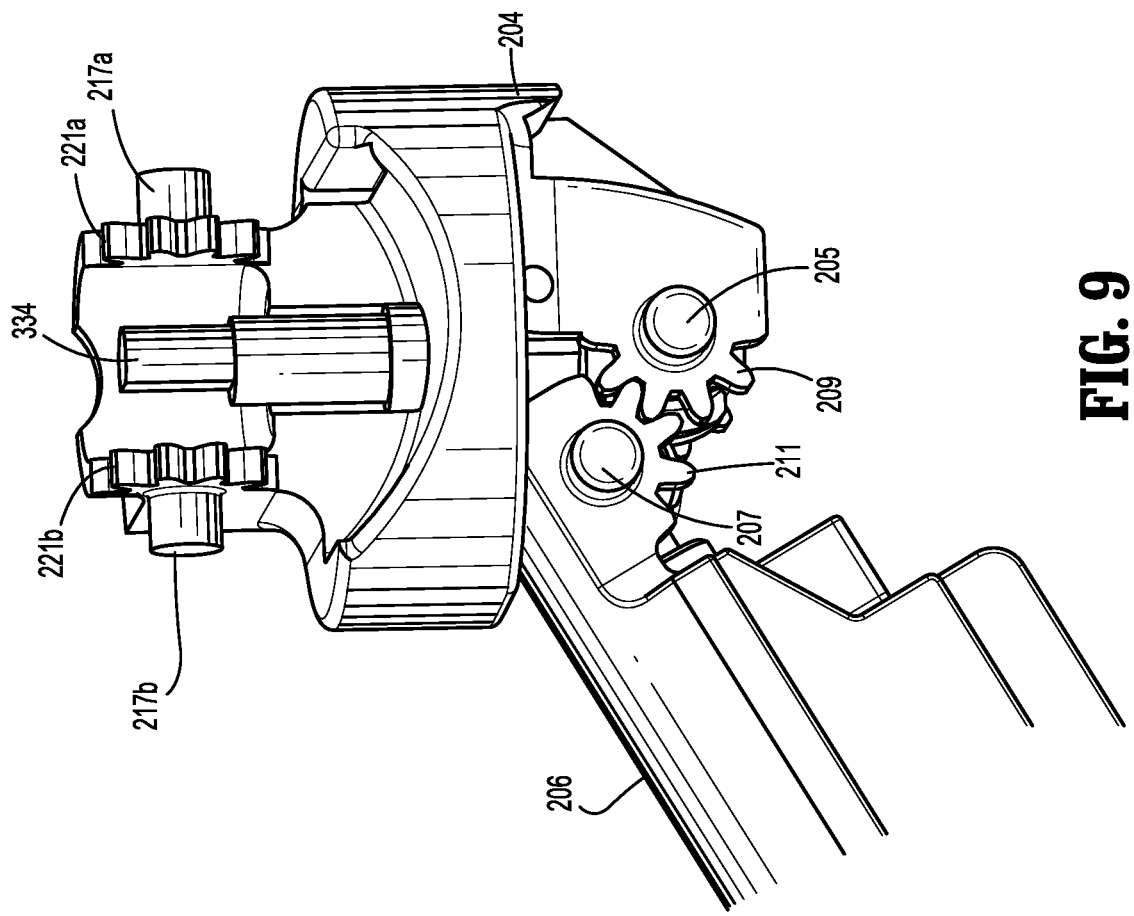
FIG. 9 is a perspective, partially-disassembled view of the proximal end of the adapter assembly of FIG. 1A with the proximal articulation mechanism in the second configuration according to the present disclosure.

With reference to FIGS. 8 and 9, each of the middle joint housing 204 and the proximal joint housing 206 includes a geared surface 209 and 211, respectively. The lever 224 maintains the geared surfaces 209 and 211 meshingly engaged allowing for the middle joint housing 204 to maintain its angular position relative to the proximal joint housing 206. In embodiments, the middle and proximal joint housings 204 and 206 may be interconnected by two levers 224, pivot pints 205 and 207 and corresponding geared surfaces 209 and 211 on two opposing sides thereof.

Figure 10:
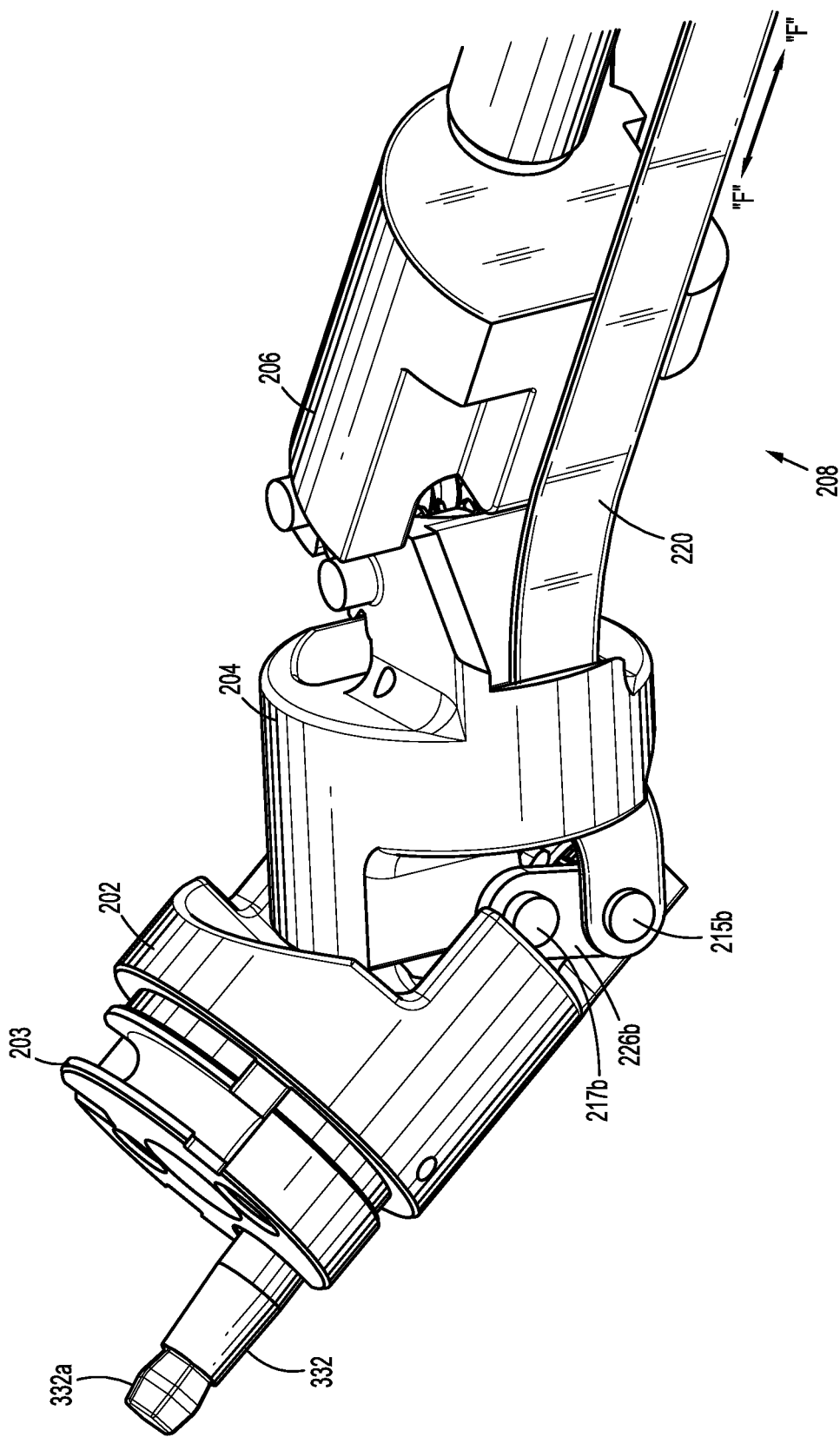
FIG. 10 is a perspective, partially-disassembled view of a distal end of the adapter assembly of FIG. 1A illustrated together with a distal articulation mechanism according to the present disclosure.

With reference to FIG. 10, distal articulation assembly 208 for pivoting distal joint housing 202 relative to middle joint housing 204 is shown. The proximal articulation assembly 212 includes the first articulation link 220 longitudinally movable within the middle and proximal joint housings 204 and 206. The middle joint housing 204 is pivotally coupled to the distal joint housing 202 via levers 226a, 226b (FIGS. 5 and 10). The levers 226a, 226b are pivotally coupled at one end to pivot pins 217a, 217b, respectively, which are disposed at a distal end of the middle joint housing 204 and at another end to pivot pins 215a, 215b, respectively, which are disposed at a proximal end of the distal joint housing 202.

The first articulation link 220 is also pivotally coupled to the pivot pin 215b. The pivot pins 217a, 217b define the pivot axis "B-B" (FIGS. 3 and 5) and act as a fulcrum for the levers 226a, 226b which pivot about the pivot pins 217a, 217b, respectively, as the first articulation link 220 is moved along a longitudinal direction "F" (FIG. 10). In particular, as the first articulation link 220 is moved in the proximal direction, as shown in FIG. 10, the distal joint housing 202 is pivoted about the pivot pins 215a, 215b along with the levers 226a, 226b, which are pivoted about the pivot pins 217a, 217b in a counterclockwise direction "D1." Distal movement of the first articulation link 220 reverses pivoting of the distal joint housing 202 in a clockwise direction "D2." The first articulation link 220 is also formed from a resilient, flexible material, such that longitudinal movement of first articulation link 220 is translated to the middle joint housing 204. The flexibility of the first articulation link 220 allows it to bend as the distal and middle joint housings 202 and 204 are articulated.

With reference to FIGS. 6-9, each of the proximal joint housing 202 and the middle joint housing 204 includes geared surfaces 219a, 219b and 221a, 221b, respectively. Levers 226a, 226b maintain the geared surfaces 219a, 219b and 221a, 221b meshingly engaged allowing for the proximal joint housing 202 to maintain its angular position relative to the middle joint housing 206.

With reference to FIGS. 5 and 11-14, the drive mechanism 330 is shown. The drive mechanism 330 includes proximal, middle, and distal transmission shafts 332, 334, 336, which transmit rotation of the rotatable connector sleeve 218 to the end effector 300. The distal, middle, and proximal transmission shafts 332, 334, 336 are disposed within proximal, middle, and distal housings 206, 204, and 202, respectively, and are configured to rotate therein. The proximal transmission shaft 336 is coupled at its proximal end to the rotatable connector sleeve 218. The proximal transmission shaft 336 includes a distal gear 336a at its distal end coupled to a proximal gear 334b of the middle transmission shaft 334. The middle transmission shaft 334 at its distal end also includes a distal gear 334a coupled to a proximal gear 332b of the distal transmission shaft 332.

Figure 11:
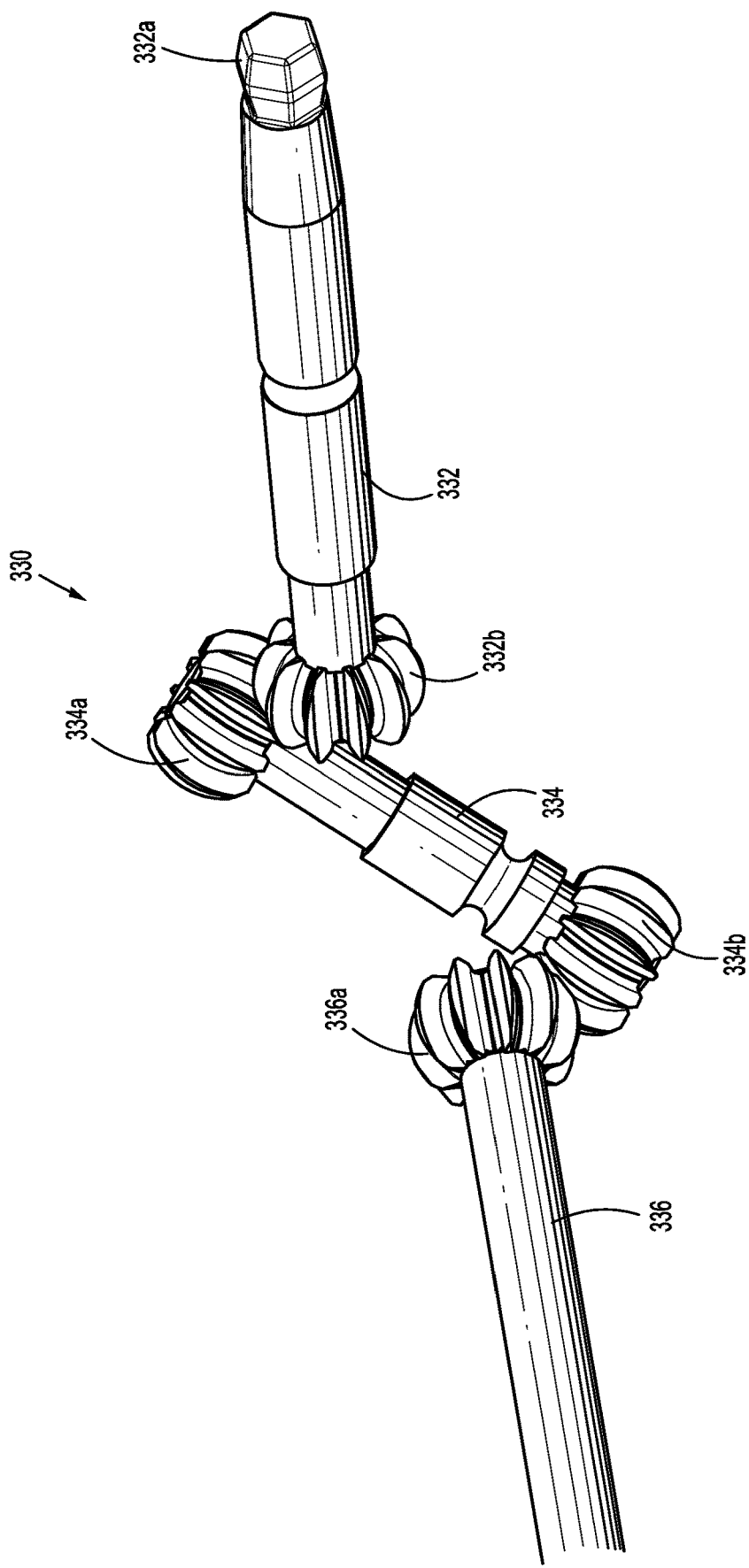
FIG. 11 is a perspective view of a drive assembly of the adapter assembly of FIG. 1A according to the present disclosure.
Figure 12:
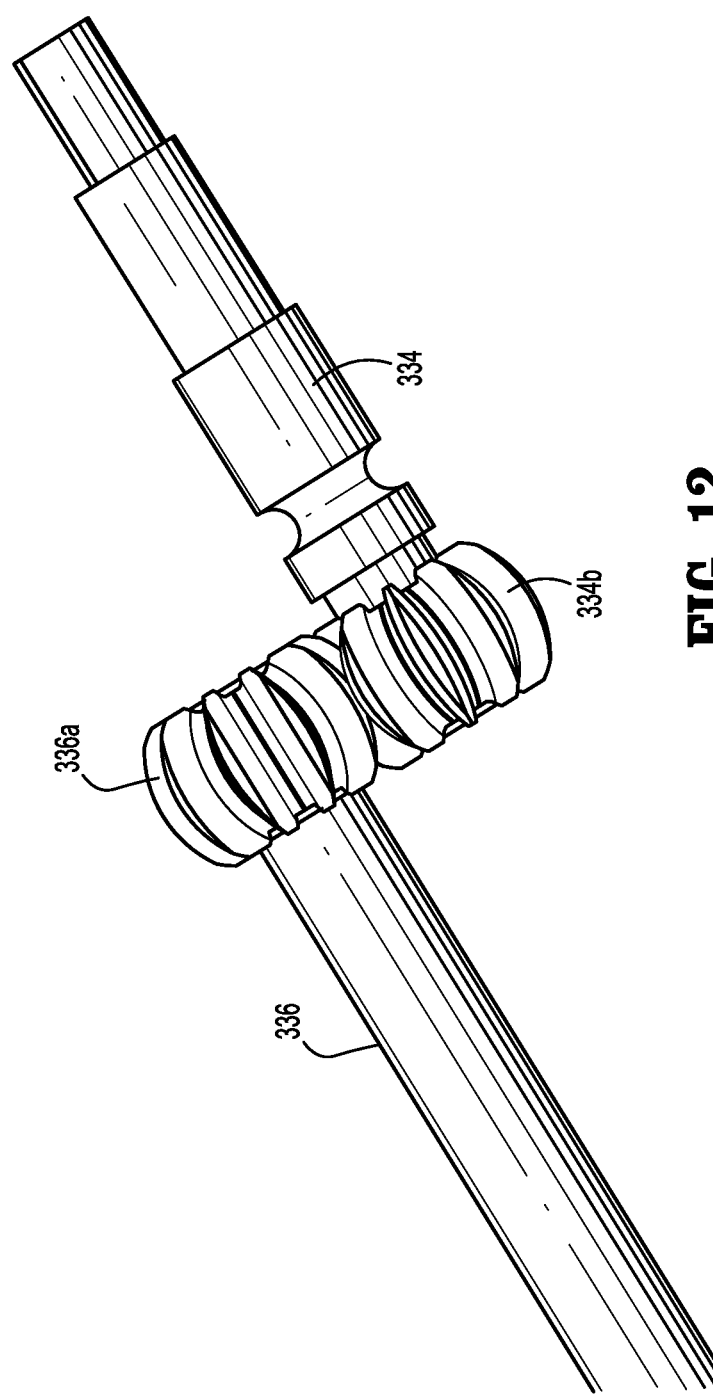
FIG. 12 is a perspective view of a middle shaft of the drive assembly of the adapter assembly of FIG. 1A according to the present disclosure.
Figure 13:
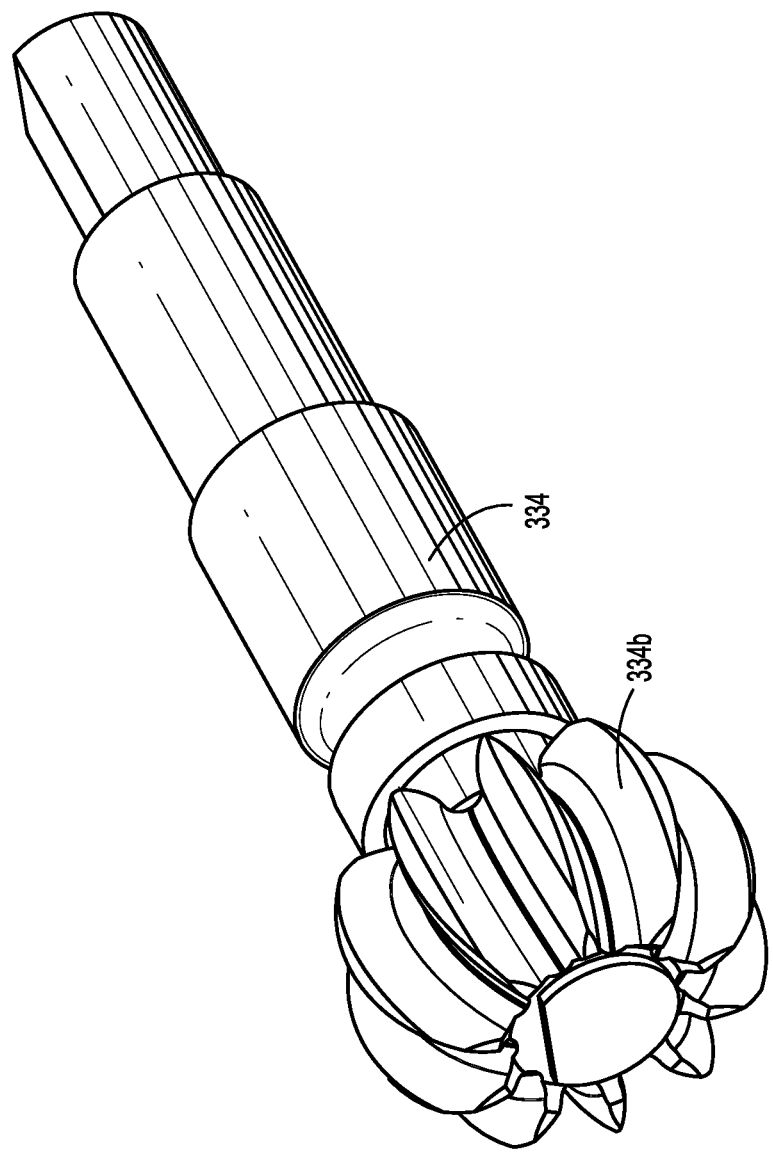
FIG. 13 is a perspective view of middle and input shafts of the drive assembly of the adapter assembly of FIG. 1A in the unarticulated configuration according to the present disclosure.
Figure 14:
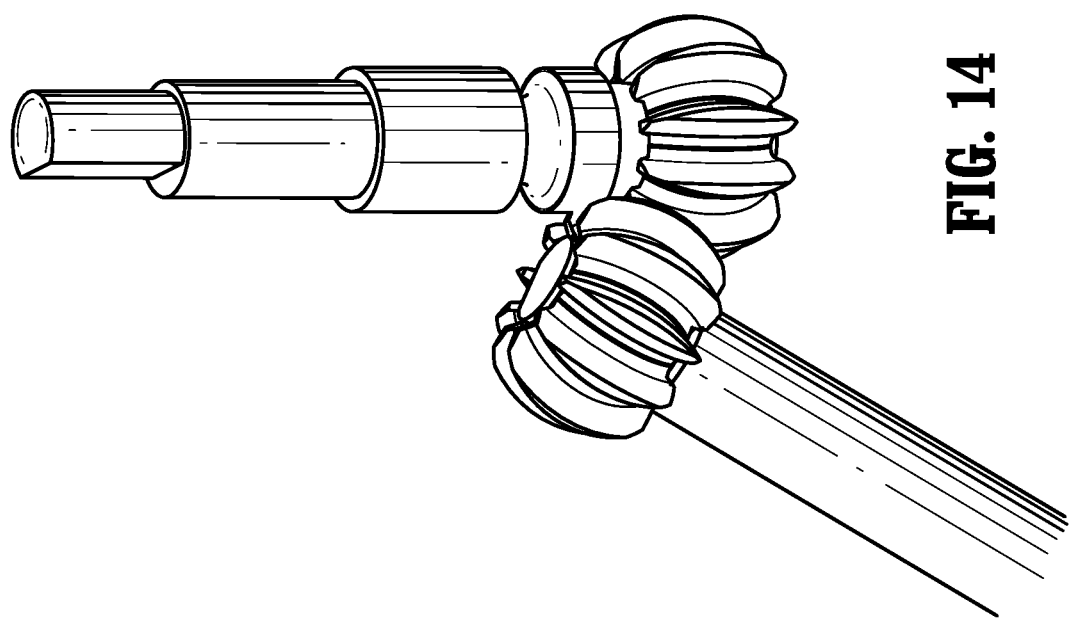
FIG. 14 is a perspective view of middle and input shafts of the drive assembly of the adapter assembly of FIG. 1A in the articulated configuration according to the present disclosure.

The gears 332b, 334a, 334b, 336a have a substantially three-dimensional ellipsoid shape (e.g., each of the teeth have a two-dimensional ellipse shape) allowing the gears 332b and 334a and gears 334b and 336a to meshingly engage each other while the transmission shafts 332, 334, 336 are pivoted relative to each other during articulation of the distal and middle joint housings 202 and 204. Each of the gears can be ball-shaped spur gears for transmitting rotary drive motion through a first, second, and third housing, such as proximal, middle, and distal joint housings 202, 204, 206. In particular, the gears 332b, 334a, 334b, 336a are disposed between the distal, middle, and proximal joint housings 202, 204, 206 allowing the gears 332b, 334a, 334b, 336a to couple the distal, middle, and proximal transmission shafts 332, 334, 336 regardless of the pivoting of the distal and middle joint housings 202 and 204, as shown in FIGS. 11, 13, and 1.

With reference to FIG. 5, the distal housing 202 also includes a flange 203 for selectively coupling the end effector 300 thereto. The distal transmission shaft 332 also includes a keyed distal end 332a dimensioned and configured to engage a connector sleeve (not shown) of the end effector 300. During operation, as the connector sleeve 218 is rotated, each of the transmission shafts 332, 334, 336 are in turn rotated via the gears 332b, 334a, 334b, 336a, which in turn, rotates the keyed distal end 332a, thereby actuating the end effector 300.

It will be understood that various modifications may be made to the embodiments disclosed herein. For example, the end effector 300 need not apply staples but rather may apply two part fasteners as is known in the art. Further, the length of the linear row of staples or fasteners may be modified to meet the requirements of a particular surgical procedure. Thus, the length of a single stroke of the actuation shaft and/or the length of the linear row of staples and/or fasteners within a disposable loading unit may be varied accordingly.

In any of the embodiments disclosed herein, the end effector can be configured to connect with adapters for hand held powered, manually powered, or robotic instruments. Furthermore the end effector can incorporate electrosurgical instruments, such as ultrasonically vibrating blades and/or clamps. The power transmission shafts and elliptical toothed gears can be used in other types of instruments, including ones for manually, robotic, motorized, hand-held or other systems. Therefore, the above description should not be construed as limiting, but merely as exemplifications of preferred embodiments. Those skilled in the art will envision other modifications within the scope and spirit of the claims appended thereto.

The invention claimed is:

1. A surgical device having a longitudinal axis, comprising:
    a proximal joint housing defining first gears;
    a middle joint housing defining second gears at a first end portion and third gears at a second, opposite end portion, the first gears meshingly engaged with the second gears;
    a distal joint housing defining fourth gears, the fourth gears meshingly engaged with the third gears;
    a first axis between the proximal and middle joint housings and defined transverse to the longitudinal axis; and
    a second axis between the middle and distal joint housing and defined transverse to the longitudinal axis, the distal joint housing being movable so as to position the second axis away from the longitudinal axis, wherein the first and second gears and the third and fourth gears maintain rotatable engagement during movement of the distal joint housing,
    wherein the proximal joint housing, the middle joint housing, and distal joint housing are rotatably coupled to one another during movement of the distal joint housing.

2. The surgical device according to claim 1, wherein the proximal and middle joint housings are connected by at least one first lever, and the middle and distal joint housings are connected by at least one second lever.

3. The surgical device according to claim 1, further including a proximal transmission shaft disposed within the proximal joint housing.

4. The surgical device according to claim 3, further including a middle transmission shaft disposed within the middle joint housing.

5. The surgical device according to claim 4, further including a distal transmission shaft disposed within the distal joint housing.

6. The surgical device according to claim 5, wherein the distal transmission shaft has a keyed distal end configured to engage an end effector of the surgical device.

7. The surgical device according to claim 5, wherein the proximal transmission shaft includes a connector sleeve disposed at a proximal portion thereof, wherein the connector sleeve is couplable to the surgical device.

8. The surgical device according to claim 5, wherein the first, second, third, and
    fourth gears define an elliptical shape along a respective longitudinal axis defined by the proximal, middle, and distal transmission shafts.

9. The surgical device according to claim 8, wherein the first, second, third, and fourth gears maintain rotatable engagement during respective movement of the proximal, middle, and distal transmission shafts.

10. A drive mechanism for a surgical device, comprising:
a proximal transmission shaft selectively couplable to the surgical device, the proximal transmission shaft defining a first gear at a distal portion thereof, a proximal portion of the proximal transmission shaft includes a connector sleeve that is couplable to the surgical device;
a middle transmission shaft having a second gear defined at a proximal portion thereof and a third gear defined at a distal portion thereof, the second gear meshingly engaged with the first gear; and
a distal transmission shaft selectively couplable to an end effector of the surgical device, the distal transmission shaft defining a fourth gear at a proximal portion thereof, the fourth gear meshingly engaged with the third gear,
wherein the first, second, third, and fourth gears maintain rotatable engagement during respective movement of the proximal, middle, and distal transmission shafts.

11. The drive mechanism according to claim 10, wherein the first, second, third, and fourth gears define an elliptical shape along a respective longitudinal axis defined by the proximal, middle, and distal transmission shafts.

12. The drive mechanism according to claim 10, wherein the drive mechanism defines a longitudinal axis along a length thereof.

13. The drive mechanism according to claim 12, wherein the drive mechanism defines a first axis between the proximal and middle transmission shafts and defined transverse to the longitudinal axis.

14. The drive mechanism according to claim 10, wherein the proximal transmission shaft is disposed within a proximal joint housing.

15. The drive mechanism according to claim 14, wherein the middle transmission shaft is disposed within a middle joint housing.

16. The drive mechanism according to claim 15, wherein the distal transmission shaft is disposed within a distal joint housing, wherein the proximal joint housing, the middle joint housing, and distal joint housing are rotatably coupled to one another during movement of the distal joint housing.

17. The drive mechanism according to claim 16, wherein the drive mechanism defines a second axis between the middle and distal joint housing and defined transverse to the longitudinal axis.

18. The drive mechanism according to claim 17, wherein the distal transmission shaft is movable so as to position the second axis away from the longitudinal axis.

19. A drive mechanism for a surgical device, comprising:
a proximal transmission shaft selectively couplable to the surgical device, the proximal transmission shaft defining a first gear at a distal portion thereof, a proximal portion of the proximal transmission shaft includes a connector sleeve that is couplable to the surgical device;
a middle transmission shaft having a second gear defined at a proximal portion thereof and a third gear defined at a distal portion thereof, the second gear meshingly engaged with the first gear; and
a distal transmission shaft selectively couplable to an end effector of the surgical device, a distal portion of the distal transmission shaft defines a keyed distal end configured to engage an end effector of the surgical device, the distal transmission shaft defining a fourth gear at a proximal portion thereof, the fourth gear meshingly engaged with the third gear,
wherein the first, second, third, and fourth gears maintain rotatable engagement during respective movement of the proximal, middle, and distal transmission shafts.

\* \* \* \* \*